(12) United States Patent
Okumu et al.

(10) Patent No.: US 7,318,931 B2
(45) Date of Patent: Jan. 15, 2008

(54) SUSTAINED RELEASE FORMULATION

(75) Inventors: Franklin Okumu, San Diego, CA (US); Jeffrey L. Cleland, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 125 days.

(21) Appl. No.: 10/176,961

(22) Filed: Jun. 21, 2002

(65) Prior Publication Data

US 2003/0045454 A1 Mar. 6, 2003

Related U.S. Application Data

(60) Provisional application No. 60/300,275, filed on Jun. 21, 2001.

(51) Int. Cl.
| | |
|---|---|
| *A61F 2/00* | (2006.01) |
| *A61F 13/00* | (2006.01) |
| *A61K 9/14* | (2006.01) |
| *A61K 38/00* | (2006.01) |
| *A61K 38/06* | (2006.01) |

(52) U.S. Cl. .............. 424/422; 424/423; 424/484; 424/489; 424/490; 514/6; 514/21

(58) Field of Classification Search .............. 424/422, 424/423, 424, 425, 426, 484, 489, 490, 491, 424/492, 493

See application file for complete search history.

(56) References Cited

U.S. PATENT DOCUMENTS

| | | | | |
|---|---|---|---|---|
| 5,589,167 A | * | 12/1996 | Cleland et al. ............ | 424/85.7 |
| 5,747,058 A | * | 5/1998 | Tipton et al. ............... | 424/423 |
| 5,851,229 A | | 12/1998 | Lentz et al. ................... | 623/1 |
| 5,981,489 A | * | 11/1999 | Stevenson et al. ............ | 514/15 |
| 6,245,806 B1 | * | 6/2001 | Dombrowski et al. ...... | 514/450 |
| 6,267,958 B1 | * | 7/2001 | Andya et al. ............ | 424/130.1 |
| 6,992,065 B2 | * | 1/2006 | Okumu ........................ | 514/21 |
| 2001/0002263 A1 | | 5/2001 | Yamagata et al. .......... | 424/486 |

FOREIGN PATENT DOCUMENTS

| | | | |
|---|---|---|---|
| EP | 0 216 485 A1 | * | 4/1987 |
| EP | 0216485 A1 | * | 4/1987 |
| EP | 0 501 375 | | 9/1992 |
| GB | 1 456 433 | | 11/1976 |
| JP | 2023866 | | 1/1990 |
| JP | 7227282 | | 8/1995 |
| WO | WO92/17200 A2 | * | 10/1992 |
| WO | WO92/17200 A2 | | 10/1992 |
| WO | WO94/12158 A1 | | 6/1994 |
| WO | WO 00/38652 A1 | * | 7/2000 |
| WO | WO 00/38652 A1 | | 7/2000 |
| WO | WO 00/78335 A1 | | 12/2000 |
| WO | WO 01/28524 A1 | | 4/2001 |

OTHER PUBLICATIONS

Bartus et al."Sustained Delivery of Proteins for Novel Therapeutic Products", Science. United States Aug. 21, 1998, vol. 281, No. 5380, pp. 1161-1162.*
Bartus, R.T., et al.: "Sustained delivery of proteins for novel therapeutic agents." Science. United States Aug. 21, 1998, vol. 281, No. 5380, pp. 1161-1162.
Smith, D.A., et al.: "A novel parenteral delivery system", Pharm. Research, NY, NY, US, vol. 13, No. 3, 1996, p. 300 XP001041946, ISSN: 0724-8741.

* cited by examiner

*Primary Examiner*—S. Tran
(74) *Attorney, Agent, or Firm*—Evan Law Group LLC

(57) ABSTRACT

A composition comprises a protein, a polyol, and a metal. The protein is stabilized by the polyol and the metal, and is protected from denaturing when in contact with an organic solvent. The polyol may be a hydrocarbon containing two or more hydroxyl groups (—OH) bonded to carbon. The metal may be divalent.

29 Claims, 1 Drawing Sheet

SUSTAINED RELEASE FORMULATION

This application claims the benefit of U.S. Provisional Application No. 60/300,275, filed Jun. 21, 2001, which is incorporated herein by reference.

BACKGROUND

Protein-based therapies can be more difficult to administer to patients than other pharmaceuticals. Because the efficacy of a protein is related to its conformation, therapeutic formulations cannot be subjected to conditions that contribute to the unfolding, or denaturing, of the protein. Special care is typically used in preparing, storing, and administering protein-based therapies. In addition to avoiding any denaturing of the protein, it is often desirable to control the amount of the protein administered to a patient over time. This helps to avoid protein concentrations within the patient that are undesirably high or that are too low to be effective. Controlled release protein-based therapies can be administered by a variety of methods, including oral delivery of tablets or capsules, inhalation of powders, and implantation of depots from which the protein is gradually released.

The preparation of these formulations typically includes mixing the protein with an organic solvent. For example, a powder formulation may be made by spraying a mixture of the protein and an organic solvent into liquid nitrogen. Alternatively, the protein may be mixed with a solution of a bioerodible polymer in an organic solvent, with formation of microparticles which contain the protein and the polymer by coagulation of the mixture. Furthermore, proteins, powdered formulations, or microparticles can be mixed with an organic solvent to produce a liquid or gel which may be injected into a patient. A drawback to the use of organic solvents is their tendency to cause protein denaturing.

Additives have been used to stabilize proteins in the presence of a denaturing organic solvent. These additives include surfactants (U.S. Pat. No. 5,096,885), amino acids (U.S. Pat. No. 4,297,344), polyols (U.S. Pat. No. 5,589,167), natural polymers (WO 8903671), synthetic polymers (Pharm. Res. 8:285–291, 1991), and metals (U.S. Pat. No. 6,191,107 B1).

There is a need for improved stabilization of proteins during the preparation, storage, and administration of protein-based therapies. Protein formulations which have good stability in organic solvents would be useful in a wide variety of controlled release applications.

BRIEF SUMMARY

In a first aspect, the present invention is a composition comprising a protein, a polyol, and a metal.

In a second aspect, the present invention is a method of administering a protein, including injecting the above composition into a patient in need of the protein.

In a third aspect, the present invention is a method of making a sustained release composition, comprising mixing a complex and a liquid carrier to form said sustained release composition. The liquid carrier comprises sucrose acetate isobutyrate; and the complex comprises a protein, a polyol, and zinc.

In a fourth aspect, the present invention is a kit containing a container, a protein, a polyol, a metal, and a liquid carrier. The liquid carrier comprises sucrose acetate isobutyrate.

In a fifth aspect, the present invention is a composition comprising a protein, an alcohol, and a metal. The alcohol is selected from the group consisting of a monosaccharide, a polysaccharide, glycerol, mannitol, sorbitol, inositol, and polyethylene glycol.

In a sixth aspect, the present invention is a method of administering a protein, including injecting the above composition into a patient in need of the protein.

In a seventh aspect, the present invention is a method of making a sustained release composition, comprising mixing a complex and a liquid carrier to form said sustained release composition. The liquid carrier comprises sucrose acetate isobutyrate; and the complex comprises a protein, an alcohol, and zinc. The alcohol is selected from the group consisting of a monosaccharide, a polysaccharide, glycerol, mannitol, sorbitol, inositol, and polyethylene glycol.

In a eighth aspect, the present invention is a kit containing a container, a protein, an alcohol, a metal, and a liquid carrier. The liquid carrier comprises sucrose acetate isobutyrate. The alcohol is selected from the group consisting of a monosaccharide, a polysaccharide, glycerol, mannitol, sorbitol, inositol, and polyethylene glycol.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION

Figure 1:
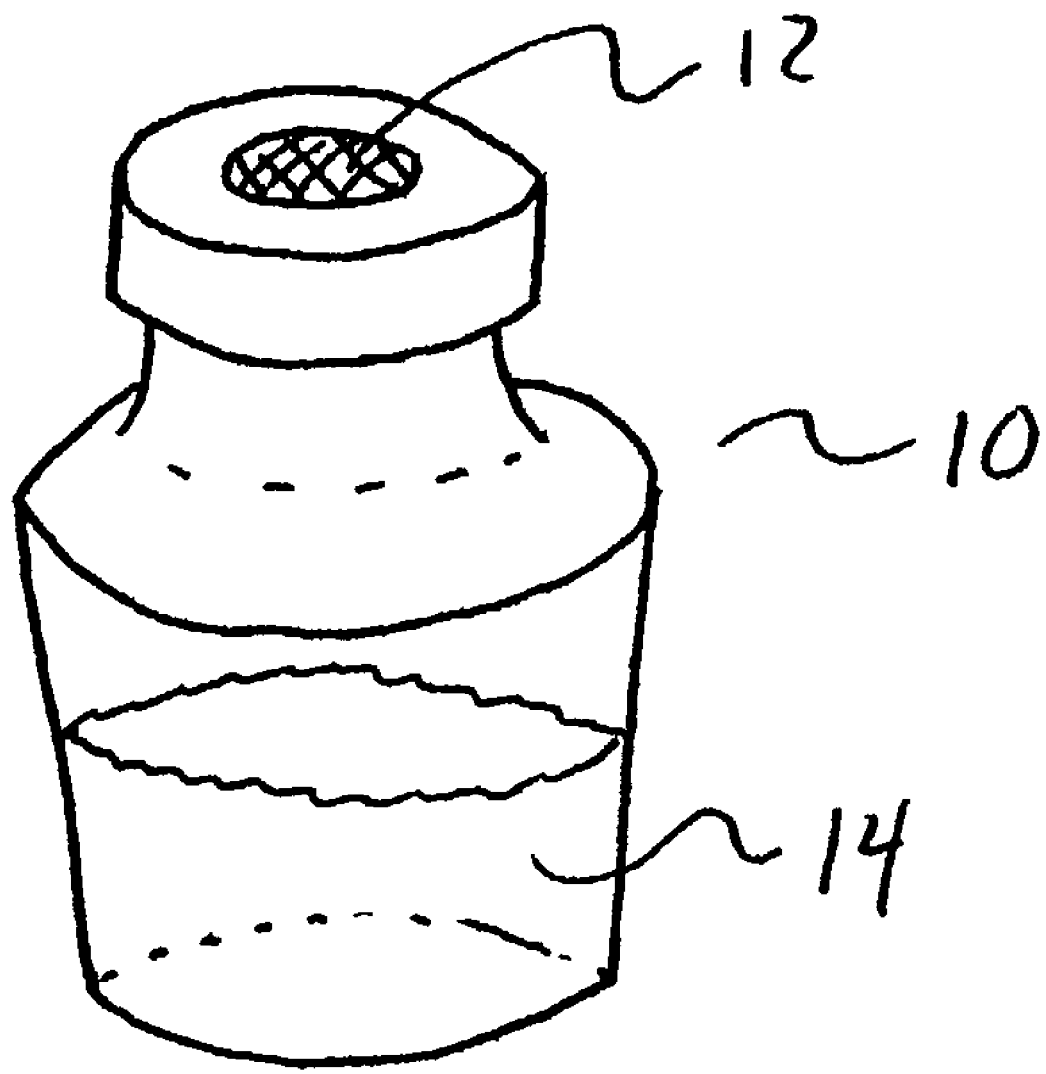
FIG. 1 is a view of a vial containing an injectable composition.

The present invention includes stabilization of a protein with a polyol and a metal, protecting the protein from denaturing when in contact with an organic solvent. The degree of retention of the native protein conformation is a surprising and unexpected effect of the combination of a protein with both a polyol and a metal. The polyol and metal together provide a synergistic protection of the protein conformation and activity which is greater than what would be expected from the effect that either the polyol or the metal have separately.

The polyol is an alcohol, and may be any hydrocarbon containing two or more hydroxyl groups (—OH) bonded to carbon, where hydrocarbon refers to a compound containing carbon and hydrogen, which may also contain heteroatoms such as oxygen, nitrogen, sulfur, phosphorus, and halogen. The term polyol excludes those compounds which do not provide for a monomer recovery of at least 40%, according to the following test:

A mixture of recombinant human growth hormone (rhGH, GENENTECH, S. San Francisco, Calif.) in 25 mM sodium bicarbonate (25 mg rhGH/mL) is combined with zinc acetate to provide a 10:1 molar ratio of zinc to growth hormone. To this mixture is added 1 percent by weight (wt %) of the polyol to be tested. A 1.0 mg sample of this mixture is then added to N-methyl pyrrolidone (NMP), providing a ratio of protein mass (mg) to volume of solvent (mL) of 5 mg/mL. The resulting mixture is homogenized for 2 min at 8,000 rpm with a shear homogenizer tip and then incubated at 37° C. for 24 hours. The rhGH is recovered by dilution into a 10-fold excess of a stabilizing buffer (5 mM EDTA, 50 mM HEPES, 0.01% $NaN_3$, pH 8.0). The amount and quality of the protein recovered in this step is then determined by size exclusion chromatography-high performance liquid chromatography (SEC-HPLC), using a 7.8×300 mm TSK 2000-SWXL column at room temperature, with a mobile phase of 50 mM NaH$_2$PO$_4$, 150 mM NaCl, pH 7.2, a flow rate of 1.0 ml/min, and a run time of 20 min. Protein (10 µg) is injected and the eluent monitored for absorbance at 214 nm.

Examples of polyols include monosaccharides, such as glucose, fructose, and ribose, including cyclic isomers; glycerol; mannitol; sorbitol; inositol; polysaccharides, including disaccharides such as sucrose, trehalose, lactose, maltose, and cellobiose, and trisaccharides such as 3-fucosyllactose and blood group B trisaccharide; and polyethers such as polyethylene glycols (PEG's). The term "polyether" means a hydrocarbon containing three or more ether bonds (C—O—C). The polyol may be substituted. "Substituted" means that the moiety contains at least one, preferably 1–3 substituent(s). Suitable substituents include ether (—O—C—), amino (—NH$_2$), oxy (—O—), carbonyl (>C=O), thiol, and the like. Preferably, the polyol is mannitol, trehalose, or a polyethylene glycol. Preferred polyethylene glycols have a molecular weight, as measured by size exclusion chromatography (SEC) from 400 kDa to 8,000 kDa. More preferably, the polyethylene glycol has a molecular weight from 400 kDa to 3,500 kDa. It is preferred that the polyol has molecular weight less than about 70,000 kDa.

The relative amounts of protein and polyol in a formulation may be chosen to minimize protein denaturing. For a given protein, the ideal ratio may vary depending on the polyol used. Preferably, the mass ratio of trehalose to protein is from 100:1 to 1:100. More preferably, the mass ratio of trehalose to protein is from 1:1 to 1:10. Even more preferably, the mass ratio of trehalose to protein is from 1:3 to 1:4. Preferably, the mass ratio of mannitol to protein is from 100:1 to 1:100. More preferably, the mass ratio of mannitol to protein is from 1:1 to 1:10. Even more preferably, the mass ratio of mannitol to protein is from 1:1 to 1:2. Preferably, the mass ratio of PEG to protein will be from 100:1 to 1:100. More preferably, the mass ratio of PEG to protein is from 1:1 to 1:10.

The metal is preferably divalent. More preferably, the metal is zinc. The metal may be added to the protein by mixing an aqueous solution of the protein with a metal complex. For example, a zinc complex such as zinc acetate, zinc oxide, or zinc carbonate may be added to a solution or suspension of the protein in a buffer. Preferably, the molar ratio of metal to protein is from 1:1 to 100:1. More preferably, the molar ratio of metal to protein is from 1:1 to 20:1. Even more preferably, the molar ratio of metal to protein is from 1:1 to 10:1.

Proteins useful in the present invention include, for example, molecules such as cytokines and their receptors, as well as chimeric proteins comprising cytokines or their receptors, including, for example tumor necrosis factor alpha and beta, their receptors (TNFR-1; Gray et al., (1990) Proc. Natl. Acad. Sci. USA 87:7380–7384; and TNFR-2; Kohno et al., (1990) Proc. Natl. Acad. Sci. USA 87:8331–8335) and their derivatives; renin; growth hormones, including human growth hormone, bovine growth hormone, methione-human growth hormone, des-phenylalanine human growth hormone, and porcine growth hormone; growth hormone releasing factor (GRF); parathyroid and pituitary hormones; thyroid stimulating hormone; human pancreas hormone releasing factor; lipoproteins; colchicine; prolactin; corticotrophin; thyrotropic hormone; oxytocin; vasopressin; somatostatin; lypressin; pancreozymin; leuprolide; alpha-1-antitrypsin; insulin A-chain; insulin B-chain; proinsulin; follicle stimulating hormone; calcitonin; luteinizing hormone; luteinizing hormone releasing hormone (LHRH); LHRH agonists and antagonists; glucagon; clotting factors such as factor VIIIC, factor IX, tissue factor, and von Willebrands factor; anti-clotting factors such as Protein C; atrial natriuretic factor; lung surfactant; a plasminogen activator other than a tissue-type plasminogen activator (t-PA), for example a urokinase; bombesin; thrombin; hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; gonadotropin releasing hormone; bovine somatotropin; porcine somatotropin; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, 4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, -lamma, and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV-1 envelope glycoprotein, gp120, gp160 or fragments thereof; transport proteins; homing receptors; addressins; fertility inhibitors such as the prostaglandins; fertility promoters; regulatory proteins; antibodies and chimeric proteins, such as immunoadhesins; analogs and derivatives of these compounds, and pharmaceutically acceptable salts of these compounds, or their analogs or derivatives.

Preferably, the protein contains up to 120 amino acids per single chain. Preferably, the protein is capable of complexing with a metal. Protein-metal complexation has a dissociation constant ($K_D$) on the order of micromolar (µM) or smaller, as measured in water at physiological temperature and pH. The value $K_D$ is defined as the product of the concentration of the uncomplexed metal and the uncomplexed protein, divided by the concentration of the protein-metal complex. A non-specific interaction between a protein and a metal under the same conditions has a $K_D$ on the order of millimolar (mM). Preferably, the protein-metal complex has a $K_D$ of 0.1 µM or smaller. More preferably, the protein-metal complex has a $K_D$ of 0.01 µM or smaller.

More preferably, the protein is a growth hormone, such as human growth hormone (hGH), recombinant human growth hormone (rhGH), bovine growth hormone, methione-human growth hormone, des-phenylalanine human growth hormone, and porcine growth hormone; insulin, insulin A-chain, insulin B-chain, and proinsulin; or a growth factor, such as vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

Formulations of proteins which are stabilized with a polyol and a metal may also contain other ingredients. These ingredients include, for example, preservatives, antioxidants, bulking agents, surfactants, chelating agents, emulsifying agents, and other excipients. The term "excipient" refers to a non-therapeutic agent added to a pharmaceutical composition to provide a desired consistency or stabilizing effect. Preservatives include, for example, phenol, benzyl alcohol, metacresol, methyl paraben, propyl paraben, benzalconium chloride, and benzethonium chloride. Surfactants include, for example, POLYSORBATE 20 and 80.

The protein, polyol, and metal, together with any other ingredients, may be combined in a single step or in two or more steps. Preferably, the protein is complexed with the metal before addition of the polyol. For example, the protein, polyol, metal, and optional ingredients may be mixed in an aqueous buffer to form a solution, emulsion, or suspension. Useful buffers include, for example, phosphate, Tris, citrate, succinate, acetate, and histidine buffers. Typically, the buffer is in the range of about 2 mM to about 100 mM. Preferred buffers include sodium succinate and potassium phosphate buffers.

The aqueous formulation of protein, polyol, and metal may be used to administer the protein-based therapy, or the formulation may be further processed. For example, the formulation may be converted into a solid by lyophilization or freeze-drying, or it may be incorporated into a bioerodible polymer. A bioerodible polymer decomposes when placed inside an organism, as measured by a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC. Useful bioerodible polymers include polyesters, such as poly(caprolactone), poly(glycolic acid), poly(lactic acid), and poly(hydroxybutryate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof. Proteins may be incorporated into bioerodible polymers by formation of monolithic implants, which are surgically implanted, or by formation of microparticles of the bioerodible polymer containing the protein.

The composition may also include a carrier liquid. Preferably, the formulation of protein, polyol, and metal may be mixed with a carrier liquid to be injected into a patient; however, any order of mixing these ingredients is possible. Solid formulations and microparticles may also be injected when mixed with a liquid carrier. It is preferred that the ratio of the volume of the liquid carrier to the combined mass of the protein and the metal is from 99:1 to 70:30 w/v. More preferably, the ratio of the liquid carrier to the protein and the metal is from 95:5 to 85:15 w/v. For an implant administered by injection, the liquid mixture preferably transforms into a depot upon contact with the fluid in the body. This depot is characterized by its phase separation from the physiological fluid and its increased viscosity relative to the original liquid composition. It is this depot that serves to controllably release the protein.

The liquid carrier may be a bioerodible polymer which solidifies upon administration. Alternatively, the liquid carrier may be an agent which provides a viscosity increase upon administration. Examples of these agents include hyaluronic acid, as well as sucrose acetate isobutyrate (SAIB) as used in the SABER system (SOUTHERN BIO-SYSTEMS, Birmingham, Ala.). The SABER system is an injectable drug delivery system which is composed of a non-polymeric liquid material and an organic solvent (U.S. Pat. No. 5,747,058; Smith and Tipton (1996) Pharmaceutical Research 13(3):300). SABER is injected as a low viscosity liquid that increases rapidly in viscosity after injection. The resulting high viscosity matrix is adhesive, biodegradable and biocompatible.

The non-polymeric liquid material in the SABER system is a non-water soluble liquid having a viscosity of at least 5,000 centipoise (cP) at 37° C. which does not crystallize neat under ambient physiological conditions. The viscosity of the liquid can be measured using a CANON-FENSKE viscometer at a temperature of 25° C. The kinematic viscosity of the SABER composition, including the liquid material and the solvent, is preferably less than 1000 cP at room temperature. More preferably, the kinematic viscosity of the SABER composition is less than 200 cP at room temperature. Suitable liquid materials include stearate esters, stearate amides, long-chain fatty acid amides, long-chain fatty alcohols, long-chain esters, and disaccharide esters. Preferably, the liquid material is acetylated sucrose distearate, disaccharide acetate butyrate, or SAIB. The weight ratio of liquid material to solvent is preferably from 50:50 to 85:15 w/w. More preferably, the weight ratio of liquid material to solvent is from 50:50 to 70:30 w/w.

These formulations typically also include one or more organic solvents, such as methylene chloride, ethyl acetate, dimethyl sulfoxide (DMSO), tetrahydrofuran (THF), dimethylformamide (DMF), ethanol (EtOH), N-methyl pyrrolidone (NMP), benzyl benzoate, benzyl alcohol, miglyol, and propylene carbonate. The stability of a protein in the presence of an organic solvent is measured by recovering the protein from the solvent and measuring the percentage of the protein which is intact (ie. not denatured). Protein that is not denatured is referred to as monomer, since denatured proteins tend to aggregate together. The percentage of monomer can be measured by HPLC-SEC. Preferably, the percentage of monomer recovered is from 35% to 100%. More preferably, the percentage of monomer recovered is from 70% to 100%. Even more preferably, the percentage of monomer recovered is from 90% to 100%. Even more preferably, the percentage of monomer recovered is from 95% to 100%. Even more preferably, the percentage of monomer recovered is from 99% to 100%.

When the composition is administered in vivo, preferably less than 10% of the protein is released from the depot within 24 hours of administration, more preferably less than 5% of the protein is released from the depot within 24 hours of administration, even more preferably less than 1% of the protein is released from the depot within 24 hours of administration, even more preferably less than 0.2% of the protein is released from the depot within 24 hours of administration, even more preferably less than 0.01% of the protein is released from the depot within 24 hours of administration. The organism to which the composition is administered can be, for example, a rat or a human.

The release of the protein preferably occurs over a period of days, weeks, or months. It is preferred that at least 25% of the total amount of protein is released within one year of administration, more preferably at least 25% of the total amount of the protein is released within one month of administration, most preferably at least 25% of the total amount of the protein is released within one week of administration. Alternatively, it is preferred that at least 20% of the total amount of protein is released within one year of administration, more preferably at least 20% of the total amount of the protein is released within one month of administration, most preferably at least 20% of the total amount of the protein is released within one week of administration. The desired length of the release period will vary according to the physiological treatment desired. It is preferred that the amount of protein released within a 24 hour period is from 0.01% to 5%. More preferably, the amount of protein released within a 24 hour period is from 0.05% to 3%. Even more preferably, the amount of protein released within a 24 hour period is from 1% to 3%.

The composition may be conveniently packaged in a sterile container, such as the vial 10 illustrated in FIG. 1. This container may be part of a kit which may optionally contain a sterile syringe and needle. The vial 10 may be sealed with a septum 12. This septum seals the liquid 14 and may be pierced by a needle and syringe to permit withdrawal of the mixture. The vial may contain all the ingredients necessary for the controlled release of the protein. The liquid composition in the vial preferably contains a unit dosage of the protein. It is preferred that the end user of the mixture not be required to add further ingredients or to measure the dosage prior to administration. The liquid composition may be contained in a syringe such that it can be directly administered by injection.

Alternatively, the composition may be packaged in more than one container. For example, a liquid carrier may be in one vial, and a mixture of the protein in a solvent or solvent mixture may be in another vial. The solvents and/or solvent mixture may be the same as or different from the liquid carrier. The contents of the vials may be combined and mixed, and the final composition administered by injection. In another example, the formulation of protein, polyol and metal may be in one container, and the liquid carrier may be in another container. The protein, polyol and metal may be provided together as a powder, or the protein, polyol and metal may be provided together as a tablet or capsule. The protein, polyol and metal may be combined with the liquid carrier, and the final composition administered by injection. In another example, the polyol and metal may be provided as a mixture in the liquid carrier in a vial, and the protein may be provided in a separate container. Alternatively, the protein may be provided as a mixture in the liquid carrier in a vial, and the polyol and metal may be provided in a separate container. The contents of the containers may be combined such that a liquid formulation is formed, and the final composition administered by injection.

Preferably, the packaging of the composition or its components is disposable, more preferably recyclable. It is preferred that the composition and its packaging are sterile.

EXAMPLES

Example 1

Stabilized Protein Formulations

A solid formulation of growth hormone was produced by combining rhGH (GENENTECH, S. San Francisco, Calif.) in 25 mM sodium bicarbonate (25 mg rhGH/mL) with zinc acetate to provide a 10:1 molar ratio of zinc to growth hormone. In formulations 2 and 5, the polyol was added to this mixture at the concentration indicated. In formulations 3 and 4, no zinc was added either before or after the addition of the polyol. In formulation 1, no polyol was added to the mixture of rhGH and zinc.

The effect of organic solvents on protein stability was determined by adding rhGH solid formulation (1.0 mg) to either absolute ethanol (EtOH) or N-methyl pyrrolidone (NMP). The ratio of protein mass (mg) to volume of solvent (mL) was 5 mg/mL. After protein addition, the samples were homogenized for 2 min at 8,000 rpm with a shear homogenizer tip. The resulting suspensions were allowed to incubate at 37° C. for 24 hours. The rhGH was recovered by dilution into a 10-fold excess of a stabilizing buffer (5 mM EDTA, 50 mM HEPES, 0.01% $NaN_3$, pH 8.0). The amount and quality of the protein recovered in this step was determined by size exclusion chromatography-high performance liquid chromatography (SEC-HPLC), and the results are shown in Table 1. The SEC-HPLC was run using a 7.8×300 mm TSK 2000-SWXL column at room temperature, with a mobile phase of 50 mM $NaH_2PO_4$, 150 mM NaCl, pH 7.2. The flow rate was 1.0 ml/min, and the run time was 20 min. Protein (10 µg) was injected and the eluent monitored for absorbance at 214 nm.

The criteria for a stable formulation were maximum recovery of monomeric rhGH without formation of aggregates. Control samples of each formulation were analyzed by incubation in the buffer without exposure to an organic solvent, and the results indicate that the starting material for each formulation did not contain significant amounts of aggregate.

The presence of a polyol and zinc provide superior protection against protein denaturing after exposure to ethanol and NMP. Formulations containing both a polyol and zinc yielded higher recovery of monomer than formulations stabilized with only a polyol or only zinc.

TABLE 1

Effect of organic solvents on rhGH stability

| Formulation | Polyol Concentration (wt %) | | Zinc:rhGH (molar ratio) | % Monomer Recovered (Mean ± SD) | | % Monomer Recovered (Control) |
| --- | --- | --- | --- | --- | --- | --- |
| | Mannitol | Trehalose | | EtOH | NMP | |
| 1 | 0 | 0 | 10:1 | 31 ± 8 | 37 ± 3 | 98 |
| 2 | 1 | 0 | 10:1 | 36 ± 1 | 44 ± 1 | 98 |
| 3 | 1 | 0 | 0 | 22 ± 1 | 19 ± 1 | 98 |
| 4 | 0 | 5 | 0 | 65 ± 1 | 88 ± 1 | 99 |
| 5 | 0 | 5 | 10:1 | 72 ± 1 | 89 ± 0 | 99 |

Example 2

Controlled Release Formulation

Solid formulations of growth hormone were produced by combining rhGH with zinc and/or a polyol. In formulations 12–20, rhGH in 25 mM sodium bicarbonate (20 mg rhGH/mL) was combined with zinc acetate to provide a 10:1 molar ratio of zinc to growth hormone. In formulations 12–19, the polyol was then added to the mixture at the concentration indicated. Formulations 13 and 17 additionally included 0.02% POLYSORBATE 20, which was added with the polyol. In formulations 6–11, the polyol was added to the rhGH mixture without the addition of zinc.

The effect of polyol and zinc on protein stability in a controlled release system was determined by adding rhGH formulation in SABER (100 µL) into 2 mL of release buffer. The formulation contained a 5% load of rhGH in a 80:20 mixture of SAIB and benzyl alcohol. The buffer was 50 mM HEPES, 95 mM KCl, pH 7.2. The resulting suspensions were stored at 37° C. for 24 hours. The amount and quality of the protein recovered in this step was determined by SEC-HPLC, and the results are given in Table 2. The entire release medium was analyzed by SEC-HPLC to determine total protein content and percentage of non-aggregated protein present, using a method similar to that described in Maa et. al., J. Pharm Sci. 2(87) 152–159, 1998.

Formulations containing only a polyol or only zinc allowed for significant protein denaturing, with a maximum of 91.5% monomer recovery. The presence of both a polyol and zinc effectively protected the protein from denaturing. These formulations provided approximately 99% monomer recovery. The combination of polyol and zinc also allows for acceptable release rates of the protein from the depot, with 24-hour releases between 10 and 15%.

TABLE 2

| Formulation | Polyol Concentration | | Zinc:rhGH molar ratio | % Released 1 Day | SD | % Monomer Recovered |
|---|---|---|---|---|---|---|
| | Mannitol | Trehalose | | | | |
| 6 | 1 | 0 | 0 | 17 | 5.9 | 85.4 |
| 7 | 5 | 0 | 0 | 8 | 0.1 | 89.7 |
| 8 | 10 | 0 | 0 | 36 | 0.04 | 74.7 |
| 9 | 0 | 1 | 0 | 15 | 0.2 | 83.4 |
| 10 | 0 | 5 | 0 | 6 | 0.7 | 90.5 |
| 11 | 0 | 10 | 0 | 6 | 0.2 | 91.5 |
| 12 | 1 | 0 | 10:1 | 12 | 0.6 | 98.8 |
| 13 | 1* | 0 | 10:1 | 10 | 3.2 | 99.1 |
| 14 | 5 | 0 | 10:1 | 12 | 1.0 | 99.2 |
| 15 | 10 | 0 | 10:1 | 10 | 0.3 | 99.2 |
| 16 | 0 | 1 | 10:1 | 10 | 0.01 | 98.9 |
| 17 | 0 | 1* | 10:1 | 10 | 0.9 | 98.9 |
| 18 | 0 | 5 | 10:1 | 15 | 2.2 | 99.2 |
| 19 | 0 | 10 | 10:1 | 14 | 1.4 | 99.2 |
| 20 | 0 | 0 | 10:1 | 12 | 1.2 | 83.9 |
| 21 | 0 | 0 | 0 | 10 | 5.3 | 91.1 |

*Additionally formulated with 0.02% POLYSORBATE 20 surfactant

Obviously, numerous modifications and variations of the present invention are possible in light of the above teachings. It is therefore to be understood that within the scope of the appended claims, the invention may be practiced otherwise than as specifically described herein.

The invention claimed is:

1. A composition, comprising:
   an organic solvent;
   a protein;
   a polyol selected from the group consisting of mannitol, trehalose and polyethylene glycol; and
   a metal cation;
   wherein the metal cation is divalent,
   the metal cation is zinc,
   the mass ratio of polyol to protein is from 100:1 to 1:100,
   the molar ratio of zinc to protein is from 1:1 to 10:1,
   the amount of polyol is from 1 to 10 weight % of the total mass of the polyol, zinc and protein,
   the polyol and zinc together provide a synergistic protection of the protein conformation and activity, and
   the polyol and zinc together provide superior protection against protein denaturing after exposure to an organic solvent selected from the group consisting of ethanol, NMP and benzyl alcohol.

2. The composition of claim 1, wherein the mass ratio of polyol to protein is from 1:1 to 1:10.

3. The composition of claim 1, wherein the protein is selected from the group consisting of a growth hormone, insulin, and a growth factor.

4. The composition of claim 1, further comprising a carrier material;
   wherein the carrier material comprises a non-polymeric, non-water soluble liquid material having a viscosity of at least 5,000 cP at 37° C. that does not crystallize neat under ambient physiological conditions.

5. The composition of claim 4, wherein the liquid material is a stearate ester, a stearate amide, a long-chain fatty acid amide, a long-chain fatty alcohol, a long-chain ester, or a disaccharide ester.

6. The composition of claim 4, wherein the liquid material is acetylated sucrose distearate.

7. The composition of claim 4, wherein the liquid material is disaccharide acetate butyrate.

8. The composition of claim 4, wherein the liquid material is sucrose acetate isobutyrate.

9. The composition of claim 4, wherein the composition has a viscosity less than 1000 cP at room temperature.

10. The composition of claim 4, solvent, wherein the composition has a viscosity less than 200 cP at room temperature.

11. A method of administering a protein, comprising:
    injecting the composition of claim 1 into a patient in need of said protein.

12. The method of claim 11, wherein less than 0.2% of the protein is released within 24 hours of administration.

13. The method of claim 11, wherein the percentage of the protein released within a 24 hour period is from 0.05% to 3%.

14. The method of claim 11, wherein the percentage of the protein released within a 24 hour period is from 1% to 3%.

15. A method of making a sustained release composition, comprising:
    mixing a complex and a liquid carrier to form said sustained release composition;
    wherein said liquid carrier comprises sucrose acetate isobutyrate and an organic solvent; and
    wherein said complex comprises
      a protein,
      a polyol selected from the group consisting of mannitol, trehalose and polyethylene glycol, and zinc,
    the mass ratio of polyol to protein is from 100:1 to 1:100,
    the molar ratio of zinc to protein is from 1:1 to 10:1,
    the amount of polyol is from 1 to 10 weight % of the total mass of the polyol, zinc and protein,
    the polyol and zinc together provide a synergistic protection of the protein conformation and activity, and
    the polyol and zinc together provide superior protection against protein denaturing after exposure to an organic solvent selected from the group consisting of ethanol, NMP and benzyl alcohol.

16. The method of claim 15, wherein said sustained release composition has a viscosity less than 1000 cP at room temperature.

17. The method of claim 15, wherein said sustained release composition has a viscosity less than 200 cP at room temperature.

18. The method of claim 15, wherein said solvent is ethanol, benzyl benzoate, miglyol, propylene carbonate, or benzyl alcohol.

19. The method of claim 15, wherein the ratio of sucrose acetate isobutyrate to solvent is from 50:50 w/w to 85:15 w/w.

20. The method of claim 15, wherein the ratio of sucrose acetate isobutyrate to solvent is from 50:50 w/w to 70:30 w/w.

21. The method of claim 15, wherein said sustained release composition comprises:
   a sucrose acetate isobutyrate to solvent ratio from 50:50 w/w to 85:15 w/w, wherein the sucrose acetate isobutyrate and solvent together form said liquid carrier; and
   a liquid carrier to complex ratio from 95:5 w/v to 85:15 w/v.

22. The method of claim 21, wherein the ratio of sucrose acetate isobutyrate to solvent is from 50:50 w/w to 70:30 w/w.

23. A kit, comprising:
   a container;
   a protein;
   a polyol selected from the group consisting of mannitol, trehalose and polyethylene glycol;
   a metal cation;
   an organic solvent; and
   a liquid carrier;
   wherein the liquid carrier comprises sucrose acetate isobutyrate;
   wherein the metal cation is divalent,
   the metal cation is zinc,
   the mass ratio of polyol to protein is from 100:1 to 1:100,
   the molar ratio of zinc to protein is from 1:1 to 10:1,
   the amount of polyol is from 1 to 10 weight % of the total mass of the polyol, zinc and protein,
   the polyol and zinc together provide a synergistic protection of the protein conformation and activity, and
   the polyol and zinc together provide superior protection against protein denaturing after exposure to an organic solvent selected from the group consisting of ethanol, NMP and benzyl alcohol.

24. The kit of claim 23, comprising a unit dosage of the protein.

25. The kit of claim 23, wherein the polyol, the metal cation, and the liquid carrier are sterile.

26. The kit of claim 23, further comprising a syringe.

27. The kit of claim 23, wherein the container comprises a septum.

28. The composition of claim 1, wherein when the protein is recovered from the organic solvent, from 95 to 100% of the protein is in monomer form as measured by HPLC-SEC.

29. The method of claim 11, wherein less than 10% of the protein is released within 24 hours of administration.

* * * * *